(12) United States Patent
Kim et al.

(10) Patent No.: US 11,612,442 B2
(45) Date of Patent: Mar. 28, 2023

(54) VASCULAR IMAGING DEVICE AND METHOD FOR DETECTING GUIDEWIRE BASED ON CURVE SIMILARITY LEVELS

(71) Applicant: Medipixel, Inc., Seoul (KR)

(72) Inventors: YoungEon Kim, Seoul (KR); KyoSeok Song, Seoul (KR)

(73) Assignee: Medipixel, Inc., Seoul (KR)

( * ) Notice: Subject to any disclaimer, the term of this patent is extended or adjusted under 35 U.S.C. 154(b) by 0 days.

(21) Appl. No.: 17/580,243

(22) Filed: Jan. 20, 2022

(65) Prior Publication Data

US 2022/0378512 A1    Dec. 1, 2022

(30) Foreign Application Priority Data

May 25, 2021   (KR) .......................... 10-2021-0067041

(51) Int. Cl.
*A61B 34/20*       (2016.01)
*G06V 10/74*      (2022.01)
*G06V 10/46*      (2022.01)
*G06V 10/44*      (2022.01)
*G06V 10/75*      (2022.01)

(52) U.S. Cl.
CPC ............ *A61B 34/20* (2016.02); *G06V 10/457* (2022.01); *G06V 10/46* (2022.01); *G06V 10/757* (2022.01); *G06V 10/761* (2022.01); *G06V 2201/03* (2022.01)

(58) Field of Classification Search
CPC ...... A61B 34/20; G06V 10/457; G06V 10/46; G06V 10/757; G06V 10/761; G06V 2201/03
See application file for complete search history.

(56) References Cited

FOREIGN PATENT DOCUMENTS

KR    1020200129229 A    11/2020

OTHER PUBLICATIONS

"Shape Similarity Measures, Properties and Constructions", Remco C. Veltkamp and Michiel Hagedoorn, Department of Computing Science, Utrecht University, The Netherlands {Remco.Veltkamp,mh} @cs.uu.nl pp. 1-10.
English Translation of KR Second Office Action, dated Oct. 21, 2021. pp. 1-4.

*Primary Examiner* — Serkan Akar
(74) *Attorney, Agent, or Firm* — George McGuire

(57) ABSTRACT

A method for determining a similarity between curves performed by an electronic device includes extracting a candidate curve corresponding to at least a part of a blood vessel and a source curve corresponding to a guidewire from a blood vessel image, sampling the same sampling number of points from each of the candidate curve and the source curve, calculating a similarity level between the candidate curve and the source curve based on the points sampled from the candidate curve and the points sampled from the source curve, and determining whether the candidate curve and the source curve are similar, based on the calculated similarity level.

14 Claims, 11 Drawing Sheets

VASCULAR IMAGING DEVICE AND METHOD FOR DETECTING GUIDEWIRE BASED ON CURVE SIMILARITY LEVELS

CROSS-REFERENCE TO RELATED APPLICATION

This application claims the benefit of Korean Patent Application No. 10-2021-0067041 filed on May 25, 2021, in the Korean Intellectual Property Office, the entire disclosure of which is incorporated herein by reference for all purposes.

BACKGROUND

1. Field of the Invention

One or more example embodiments relates to a guidewire detecting technique.

2. Description of the Related Art

During a treatment which is performed by inserting a surgical operation tool in a body and checking a position of the surgical operation tool through an X-ray, a structure and a position of a blood vessel are identified by injecting a contrast. However, the blood vessel is identified only for a short time after injecting the contrast. Further, the position of the blood vessel in a heart area and/or an area adjacent to the heart may be irregularly changed due to the influence of heartbeat and breathing. Accordingly, in order to periodically identify a shape of the blood vessel, the contrast may be repeatedly injected. In a cardiovascular interventional procedure, it is very important to move a guidewire to a lesion area. Even though the contrast is repeatedly injected, it is difficult to clearly identify the blood vessel until a next contrast is injected so that it may be difficult to manipulate the guidewire to reach a desired location. This is because it is difficult to identify a position of a tip of the guidewire located with respect to the blood vessel.

The above description is information the inventor(s) acquired during the course of conceiving the present disclosure, or already possessed at the time, and is not necessarily art publicly known before the present application was filed.

SUMMARY

According to an aspect, a method for determining a similarity between curves performed by an electronic device may include extracting a candidate curve corresponding to at least a part of a blood vessel and a source curve corresponding to a guidewire from a blood vessel image; sampling the same sampling number of points from each of the candidate curve and the source curve; calculating a similarity level between the candidate curve and the source curve based on the points sampled from the candidate curve and the points sampled from the source curve; and determining whether the candidate curve and the source curve are similar, based on the calculated similarity level.

The extracting may include: extracting the candidate curve corresponding to the at least a part of the blood vessel from a blood vessel image of a reference frame; and extracting the source curve corresponding to the guidewire from a blood vessel image of a target frame.

The calculating of a similarity level may include: sampling points from the candidate curve and the source curve so as to have the same interval between adjacent points.

The calculating of a similarity level may include: calculating the similarity level based on at least one of distance information and angle information between the candidate curve and the source curve.

The calculating of a similarity level may include: matching points sampled from the candidate curve to points sampled from the source curve so as not to be overlaid; and calculating distance information between the candidate curve and the source curve based on a minimum value of a sum of Euclidean distances between matched points.

The calculating of a similarity level may include: calculating an arithmetic mean of Euclidean distances between matched points as the distance information between the candidate curve and the source curve.

The calculating of a similarity level may include: calculating a distance matrix based on a Euclidean distance for each of the points sampled from the candidate curve and each of the points sampled from the source curve; and calculating the distance information from the calculated distance matrix based on the Hungarian algorithm.

The calculating of a similarity level may include: generating segments by connecting adjacent points among points sampled from the candidate curve and calculating angles between adjacent segments among the generated segments; generating segments by connecting adjacent points among points sampled from the source curve and calculating angles between adjacent segments among the generated segments; and calculating angle information between the candidate curve and the source curve using the angles calculated from the candidate curve and the angles calculated from the source curve.

The calculating of a similarity level may include: calculating the angle information using one of cross entropy and Kullback-Leibler divergence from a probability distribution of the angles calculated from the candidate curve and a probability distribution of the angles calculated from the source curve.

According to an example embodiment, the method performed by an electronic device may further include selecting a candidate curve which is the most similar to the source curve based on the calculated similarity level and determining that the guidewire is located in a blood vessel area corresponding to the selected candidate curve.

The method performed by the electronic device according to the example embodiment may further include visualizing the guidewire together with the blood vessel image by overlaying the guidewire with the blood vessel area determined that there is the guidewire.

The method performed by the electronic device according to the example embodiment may further include driving a driver based on the blood vessel area determined that the guidewire is located to move a tip of the guidewire toward a destination part.

According to another aspect, an electronic device may further include a processor configured to extract a candidate curve corresponding to at least a part of a blood vessel and a source curve corresponding to a guidewire from a blood vessel image, sample the same sampling number of points from each of the candidate curve and the source curve, calculate a similarity level between the candidate curve and the source curve based on the points sampled from the candidate curve and the points sampled from the source curve, and determine whether the candidate curve and the source curve are similar, based on the calculated similarity level.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
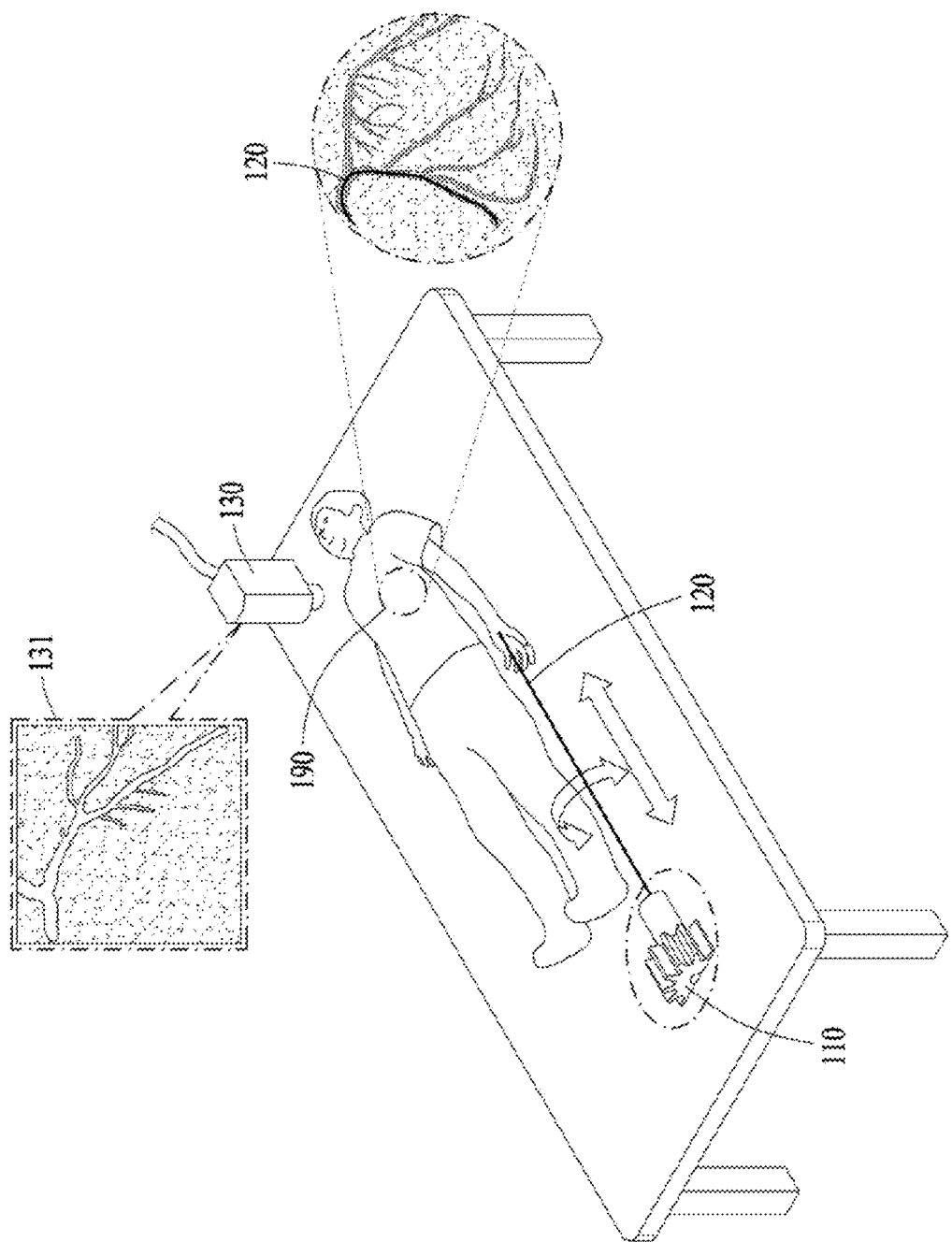
FIG. 1 illustrates a medical tool control system according to an example embodiment.

The following detailed structural or functional description is provided as an example only and various alterations and modifications may be made to the example embodiments. Here, examples are not construed as limited to the disclosure and should be understood to include all changes, equivalents, and replacements within the idea and the technical scope of the disclosure.

Terms, such as "first", "second", and the like, may be used herein to describe components. Each of these terminologies is not used to define an essence, order or sequence of a corresponding component but used merely to distinguish the corresponding component from other component(s). For example, a "first" component may be referred to as a "second" component, or similarly, and the "second" component may be referred to as the "first" component within the scope of the right according to the concept of the present disclosure.

It should be noted that if it is described that one component is "connected", "coupled", or "joined" to another component, a third component may be "connected", "coupled", and "joined" between the first and second components, although the first component may be directly connected, coupled, or joined to the second component.

The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or populations thereof.

Unless otherwise defined, all terms used herein including technical or scientific terms have the same meaning as commonly understood by one of ordinary skill in the art to which examples belong. Terms, such as those defined in commonly used dictionaries, are to be interpreted as having a meaning that is consistent with their meaning in the context of the relevant art, and are not to be interpreted in an idealized or overly formal sense unless expressly so defined herein.

Hereinafter, example embodiments will be described in detail with reference to the accompanying drawings. When describing the example embodiments with reference to the accompanying drawings, like reference numerals refer to like constituent elements and a repeated description related thereto will be omitted.

FIG. 1 illustrates a medical tool control system according to an example embodiment.

A medical tool control system according to an example embodiment is a system for controlling a movement of a medical tool 120 and may include a vascular imaging device 130 and a medical tool control device. Even though in FIG. 1, for the convenience of description, only a driver 110 of the medical tool control device is illustrated, it is not limited thereto.

The vascular imaging device 130 is a device which captures a blood vessel image 131. The blood vessel image 131 indicates an image obtained by capturing a blood vessel of a target object (for example, a subject 190). The vascular imaging device 130 captures the blood vessel image 131 using coronary angiography (hereinafter, abbreviated as "CAG") or magnetic resonance imaging (hereinafter, abbreviated as "MRI"). In the blood vessel image 131, not only the blood vessel, but also the medical tool 120 is captured together.

In the present specification, the medical tool 120 is a member which is inserted into the blood vessel, for example, may be a surgical tool which is moved and/or operated by the manipulation and/or a given instruction of an operator (for example, a doctor). For example, the medical tool 120 is a medical wire and may include a catheter and a guidewire. The catheter may refer to a medical device which provides a passage to assist the insertion or accessing of a balloon catheter and/or a guidewire in a destination affected area in the blood vessel. The catheter mainly refers to an interventional catheter having a lumen to transfer the guidewire into the blood vessel for a percutaneous treatment (for example, percutaneous vascular interventional therapy or percutaneous transluminal angioplasty). The guidewire refers to a guidance wire which guides a transfer path to allow a medical tool such as a catheter, a balloon, or a stent to reach a destination affected area through a blood vessel. For reference, the catheters may be transferred together with guidewires in major blood vessels, such as the aorta and/or coronary arteries, to reach peripheral blood vessels. The guidewire may be transferred through a lumen of the catheter and a tip of the guidewire is inserted and moved to the peripheral blood vessel. Hereinafter, in the present specification, as a medical tool, the guidewire may be mainly described, but it is not limited thereto.

The medical tool control device may move the medical tool 120 inserted into the blood vessel to a destination part in the blood vessel. Even though in FIG. 1, it is illustrated that the medical tool 120 is inserted into a blood vessel of a wrist of the subject 190, it is not limited thereto so that the medical tool may be inserted through a blood vessel of a lower body of the subject 190. A destination part may be a part in which a disease or a lesion is potentially or explicitly present.

The medical tool control device may move the tip of the medical tool 120 to the destination part. The medical tool control device may include a robot which transfers the medical tool 120. For example, the medical tool control device may transfer the medical tool 120 through the driver 110. The driver 110 may include one or more motors and a mechanical power transfer structure which converts a torque of the motor into a straight-line motion and/or a rotational motion of a desired axis. For example, the driver 110 may be driven to push the medical wire 120 in response to a forward command to allow the medical tool 120 to go forward. The driver 110 may be driven to pull the medical wire 120 in response to a backward command to allow the medical tool 120 to go backward. The driver 110 may be driven to rotate the medical wire 120 with a longitudinal axis of the medical wire 120 as a reference axis in response to the rotate command to rotate the medical tool 120. However, it is not limited thereto and the medical tool 120 may be transferred by the manipulation of the medical personnel.

The medical tool control system according to the example embodiment may provide an accurate position of the guidewire to a user (for example, a medical personnel) in an interventional therapy that uses a catheter to treat a disease of a cardiovascular, cerebrovascular, and bile duct, in a state in which an operator is spaced away from an imaging device using radiation.

The medical tool control system according to the example embodiment includes an electronic device (not illustrated) and the electronic device (not illustrated) is integrally implemented with the vascular imaging device 130 to capture a blood vessel image or receive a blood vessel image from the vascular imaging device 130. The electronic device (not illustrated) may estimate an accurate position of the guidewire according to heartbeat during the cardiovascular interventional therapy. For example, when the contrast is initially injected into the patient, the electronic device (not illustrated) automatically analyzes a structure of a blood vessel and then estimates the position of the guidewire in real-time. The electronic device (not illustrated) overlays a real-time guidewire position on the initially acquired blood vessel structure to provide an accurate position of the guidewire in the blood vessel to the user (for example, an operator) even during a time period when the contrast is not injected. Accordingly, the electronic device (not illustrated) according to the example embodiment accurately displays the position of the guidewire to reduce an amount of injected contrast and lower a skill level required for the operator. The electronic device (not illustrated) may also be referred to as a guidewire detecting device.

Figure 2:
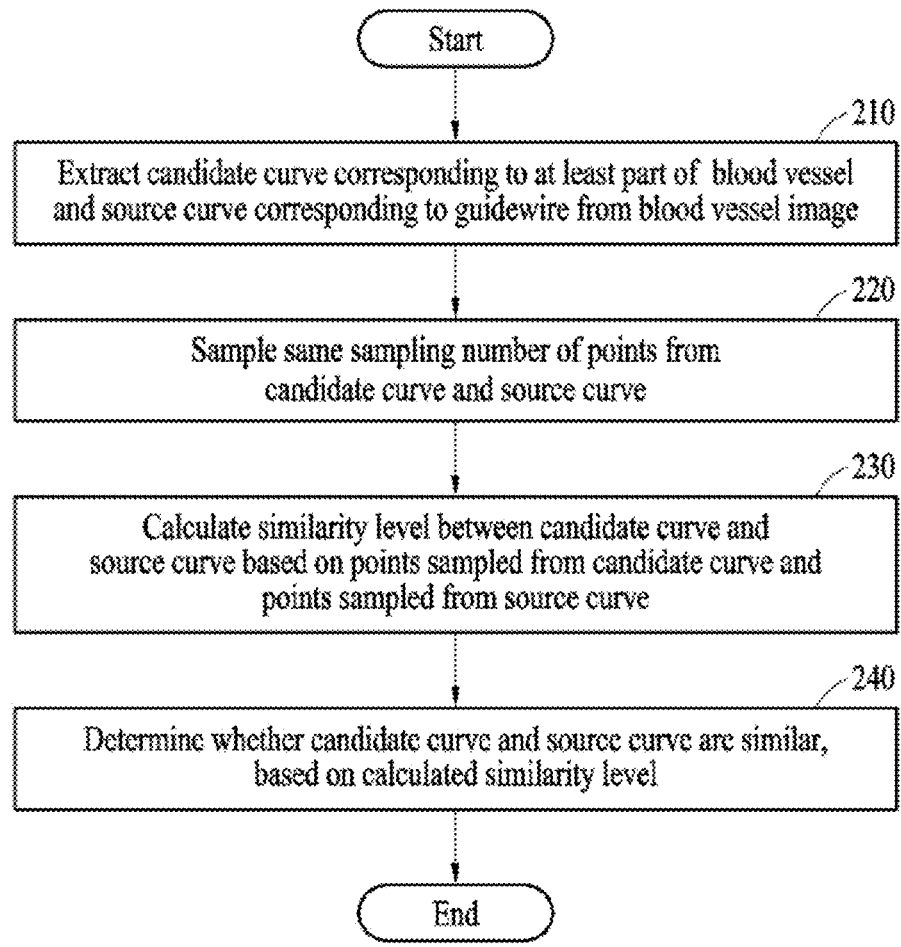
FIG. 2 explains a method for determining a similarity between curves performed by an electronic device according to an example embodiment.

FIG. 2 explains a method for determining a similarity between curves performed by an electronic device according to an example embodiment.

In step 210, the electronic device according to the example embodiment extracts a candidate curve corresponding to at least a part of the blood vessel and a source curve corresponding to the guidewire from the blood vessel image.

The electronic device may receive a blood vessel image captured by the vascular imaging device. The electronic device may extract a candidate curve corresponding to at least a part of the blood vessel from a blood vessel image of a reference frame. The electronic device may extract a source curve corresponding to the guidewire from the blood vessel image of a target frame.

For example, the electronic device analyzes a structure of a blood vessel when the contrast is injected into the patient first and then estimates the position of the guidewire in real-time. The electronic device may extract a candidate curve corresponding to at least a part of the blood vessel from a blood vessel image of a reference frame corresponding to a timing when the contrast is initially injected to the patient. The electronic device may extract a candidate curve corresponding to every blood vessel in which the guidewire can be located. In order to estimate the position of the guidewire in real-time thereafter, the electronic device may extract a source curve corresponding to the guidewire from the blood vessel image of a target frame corresponding to a timing when the position of the guidewire is estimated. However, the blood vessel image of the reference frame and the blood vessel image of the target frame are not necessarily limited to the above timing.

In step S220, the electronic device according to the example embodiment may sample the same sampling number of points from the candidate curve and the source curve, respectively. The electronic device may sample the points to have the same interval between adjacent points, from each of the candidate curve and the source curve. Here, the interval between adjacent points may indicate a distance corresponding to a part of a curve sampled from one point to the other point.

In step 230, the electronic device according to the example embodiment may calculate a similarity level between the candidate curve and the source curve based on the points sampled from the candidate curve and the points sampled from the source curve. The electronic device may calculate the similarity level based on at least one of distance information and angle information between the candidate curve and the source curve. The method of calculating the distance information and the angle information between the candidate curve and the source curve will be described below.

In step 240, the electronic device according to the example embodiment may determine whether the candidate curve and the source curve are similar to each other, based on the calculated similarity level. The electronic device may select a candidate curve having the highest similarity level to the source curve, among the candidate curves. The electronic device may determine that a blood vessel corresponding to the candidate curve having the highest similarity level is a blood vessel in which the guidewire is located. Hereinafter, the method of determining a similarity level between the candidate curve and the source curve by the electronic device will be described in more detail.

Figure 3:
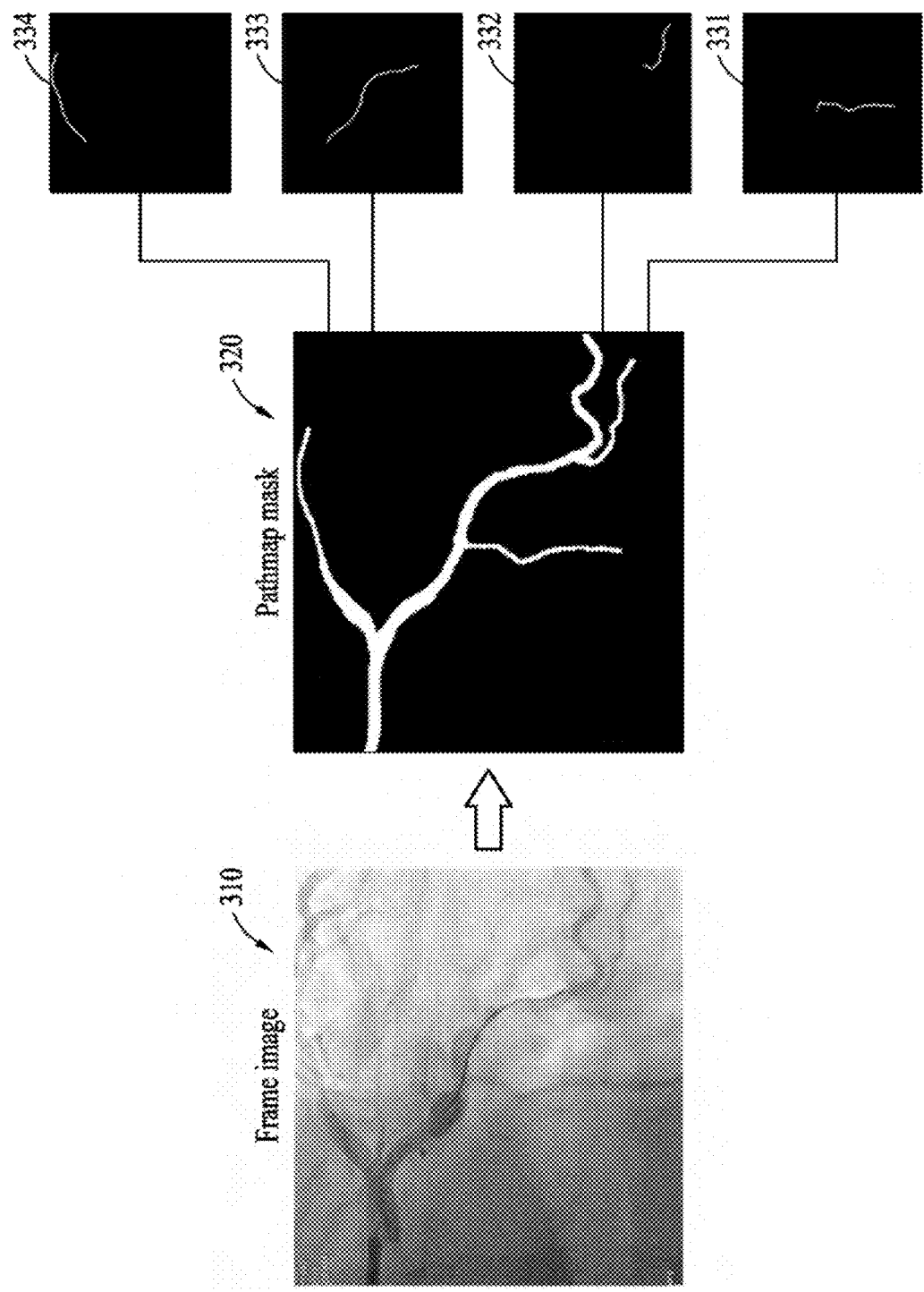
FIGS. 3 to 5 explain a process of extracting a candidate curve and a source curve from a blood vessel image by an electronic device according to an example embodiment.
Figure 4:
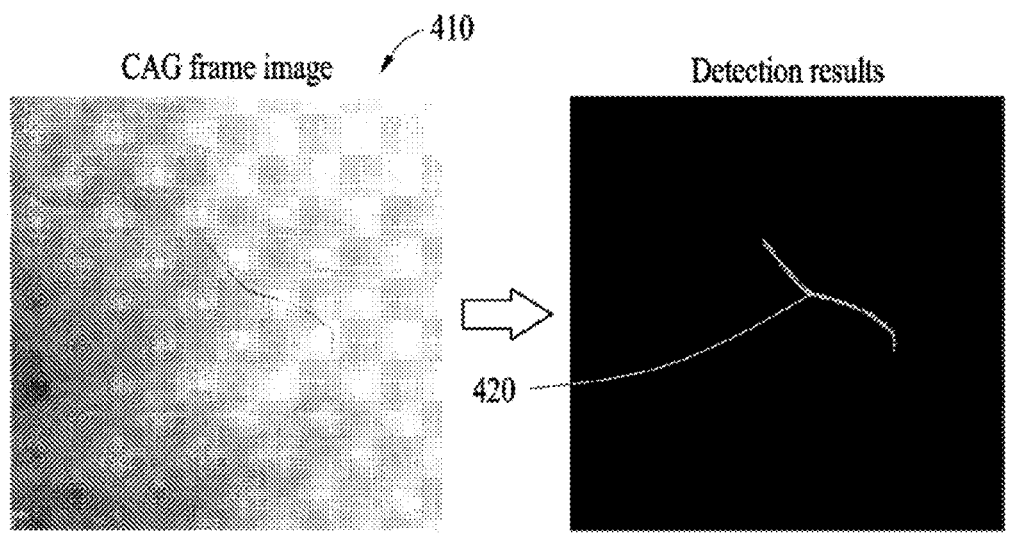
Figure 5:
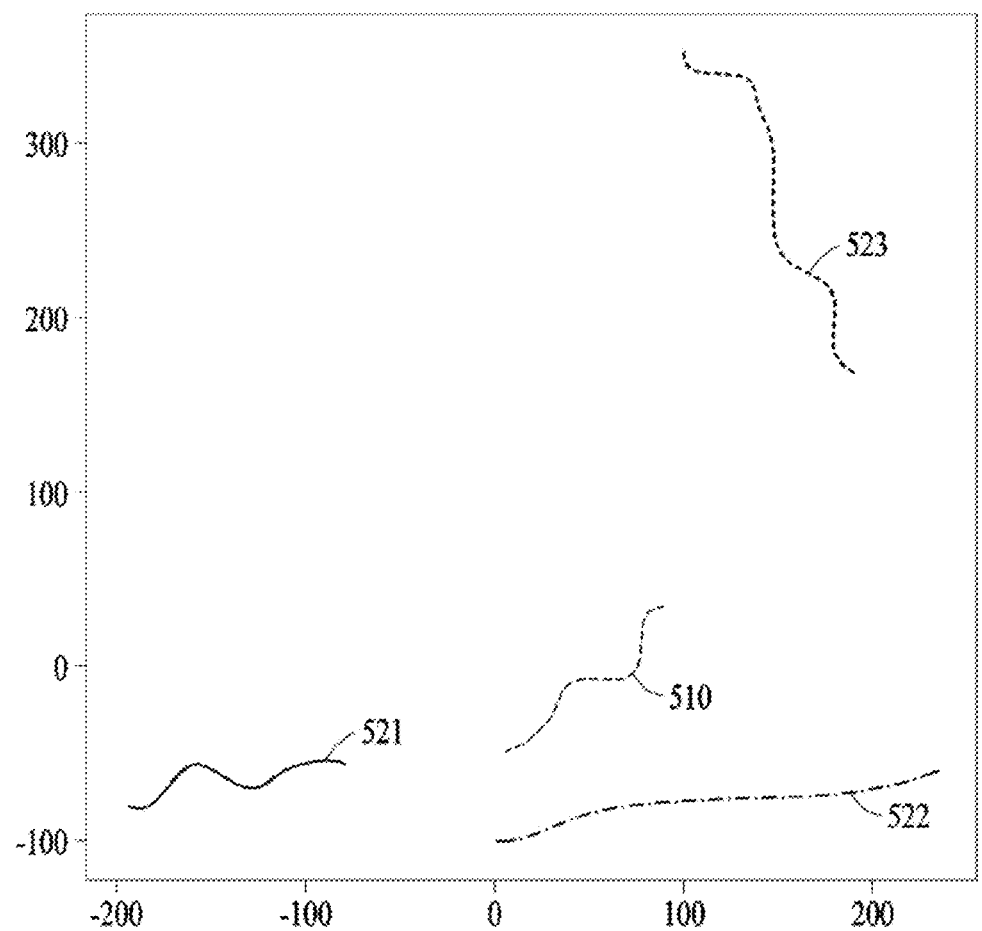

FIGS. 3 to 5 explain a process of extracting a candidate curve and a source curve from a blood vessel image by an electronic device according to an example embodiment.

FIG. 3 explains a process of extracting a candidate curve by the electronic device according to the example embodiment. The electronic device may extract a blood vessel area image 320 in which a blood vessel area is separated from the blood vessel image 310 of the reference frame. For example, as illustrated in FIG. 3, the electronic device may acquire a blood vessel area image 320 from a blood vessel image 310 (for example, a coronary angiography (CAG) image) acquired from the reference frame. The blood vessel area image 320 is an area representing an area belonging to the blood vessel and in FIG. 3, is illustrated as a masking image in which the blood vessel area is represented with white and the remaining area is represented with black, but is not limited thereto.

The electronic device may extract a blood vessel area image 320 in which a blood vessel area 320 is separated from the blood vessel image 310 of the reference frame and extract candidate curves 331, 332, 333, and 334 corresponding to at least a part of blood vessel from the blood vessel area image 320. For example, the electronic device may extract candidate curves along a centerline of at least a part of blood vessel. Even though in FIG. 3, the candidate curves 331, 332, 333, and 334 extracted so as to correspond to at least a part of the blood vessel are displayed in different images, it is not limited thereto so that the candidate curves 331, 332, 333, and 334 may be displayed in one image.

FIG. 4 explains a process of extracting a source curve corresponding to a catheter wire by the electronic device according to the example embodiment.

The electronic device according to the example embodiment may extract a source curve 420 corresponding to the guidewire from the blood vessel image 410 of the target frame (for example, a current frame). For example, the electronic device may extract guidewire information from the blood vessel image 410 of the target frame based on a machine learning model. The machine learning model is a model which is designed and trained to extract a guidewire from the blood vessel image and may include a neural network. The guidewire information is information about a part of the blood vessel image corresponding to the guidewire and may include information indicating at least one or a combination of two or more of a pixel, a point, and an area belonging to the guidewire in the image. The electronic device may extract a source curve 420 corresponding to the guidewire using guidewire information extracted based on the machine learning model. However, the method of extracting information of the guidewire by the electronic device is not necessarily limited thereto. The electronic device may extract the source curve corresponding to the guidewire from the blood vessel image 410 by various methods, without using the machine learning model.

FIG. 5 illustrates a candidate curve and a source curve extracted from the blood vessel image by the electronic device according to the example embodiment.

The electronic device according to the example embodiment may receive a blood vessel image captured by the vascular image imaging device. The electronic device may extract candidate curves 521, 522, and 523 corresponding to at least a part of the blood vessel and a source curve 510 corresponding to the guidewire from the blood vessel image. As described above, the electronic device may extract the candidate curves 521, 522, and 523 corresponding to at least a part of the blood vessel from the blood vessel image of the reference frame and extract the source curve 510 corresponding to the guidewire from the blood vessel image of the target frame. Since the blood vessel image of the reference frame and the blood vessel image of the target frame have the same resolution, the candidate curves and the source curve extracted from the blood vessel image may be displayed in one image as illustrated in FIG. 5, in consideration of the position extracted in the blood vessel image. The electronic device may calculate the distance information and the angle information between the candidate curve and the source curve to calculate the similarity level between the candidate curve and the source curve.

According to another example embodiment, the electronic device may not necessarily display the candidate curves and the source curve in one image. Instead, the electronic device may calculate the distance information and the angle information between the candidate curve and the source curve in consideration of a position (for example, an x-coordinate and a y-coordinate) of the candidate curve in the image in which the candidate curve is displayed and a position of the source curve in the image in which the source curve is displayed. For example, a distance between a first point on the candidate curve and a second point on the source curve may be calculated based on a coordinate corresponding to a position of the first point in the image and a coordinate corresponding to a position of the second point in another image.

Figure 6:
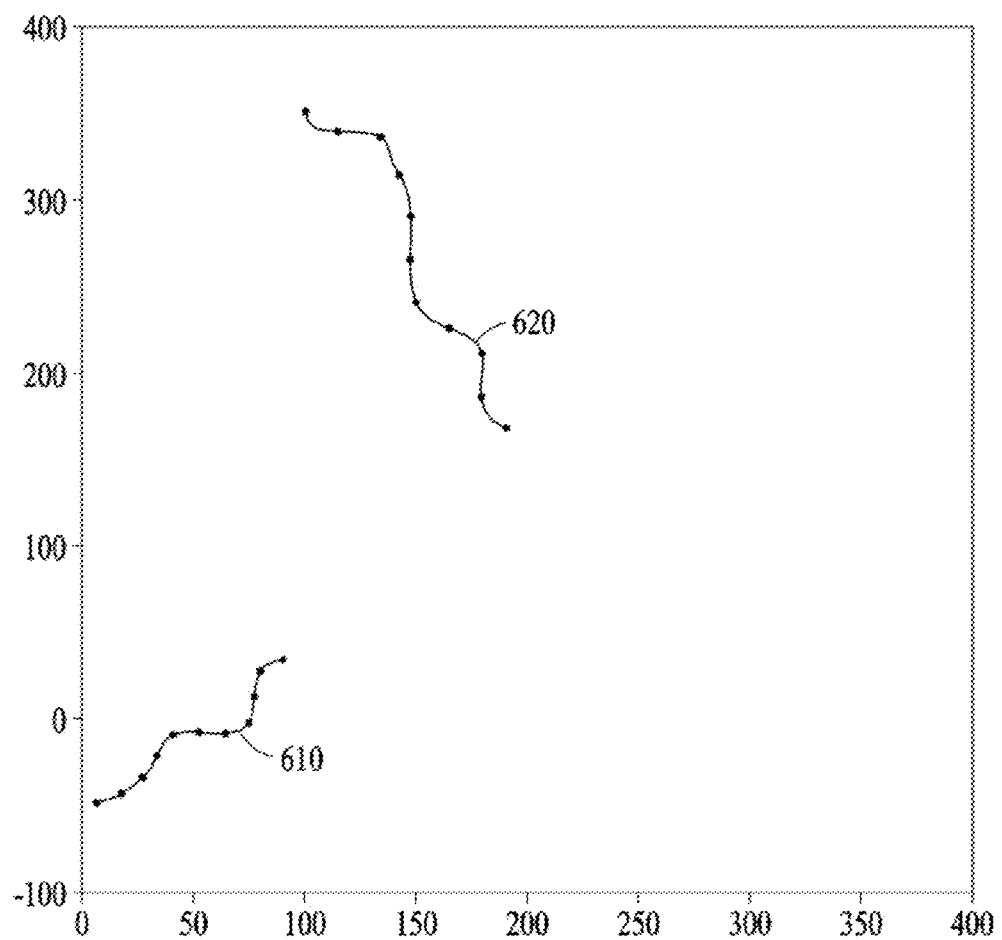
FIG. 6 illustrates a process of sampling the same sampling number of points from a candidate curve and a source curve.

FIG. 6 illustrates a process of sampling the same sampling number of points from a candidate curve and a source curve.

The electronic device according to the example embodiment may sample the same sampling numbers of points from a candidate curve 620 and a source curve 610. In FIG. 6, 50 sampling points are sampled from each of the candidate curve and the source curve, but the sampling number is not necessarily limited thereto.

When the first sampling number of points is sampled from the candidate curve, the electronic device may sample the first sampling number of points such that both ends of the candidate curve are included in the sampling points. Similarly, when the first sampling number of points is sampled from the source curve, the electronic device may sample the first sampling number of points such that both ends of the source curve are included in the sampling points.

According to the example embodiment, when one of candidate curves and the source curve are compared, the electronic device may sample a predetermined same sampling number of points at every comparison. For example, when the electronic device determines whether the first candidate curve is similar to the source curve, it is assumed that the first candidate curve and the source curve are sampled with the first sampling number of points. In this case, when the electronic device determines whether the second candidate curve which is different from the first candidate curve is similar to the source curve, the first sampling number of points may be sampled from the second candidate curve and the source curve.

According to another example embodiment, when one of candidate curves and the source curve are compared, the electronic device may not sample the same sampling number of points at every comparison. For example, when the electronic device determines whether the first candidate curve is similar to the source curve, it is assumed that the first candidate curve and the source curve are sampled with the first sampling number of points. In this case, when the electronic device determines whether the second candidate curve which is different from the first candidate curve is similar to the source curve, the second sampling number of points which is different from the first sampling number may be sampled from the second candidate curve and the source curve.

Figure 7:
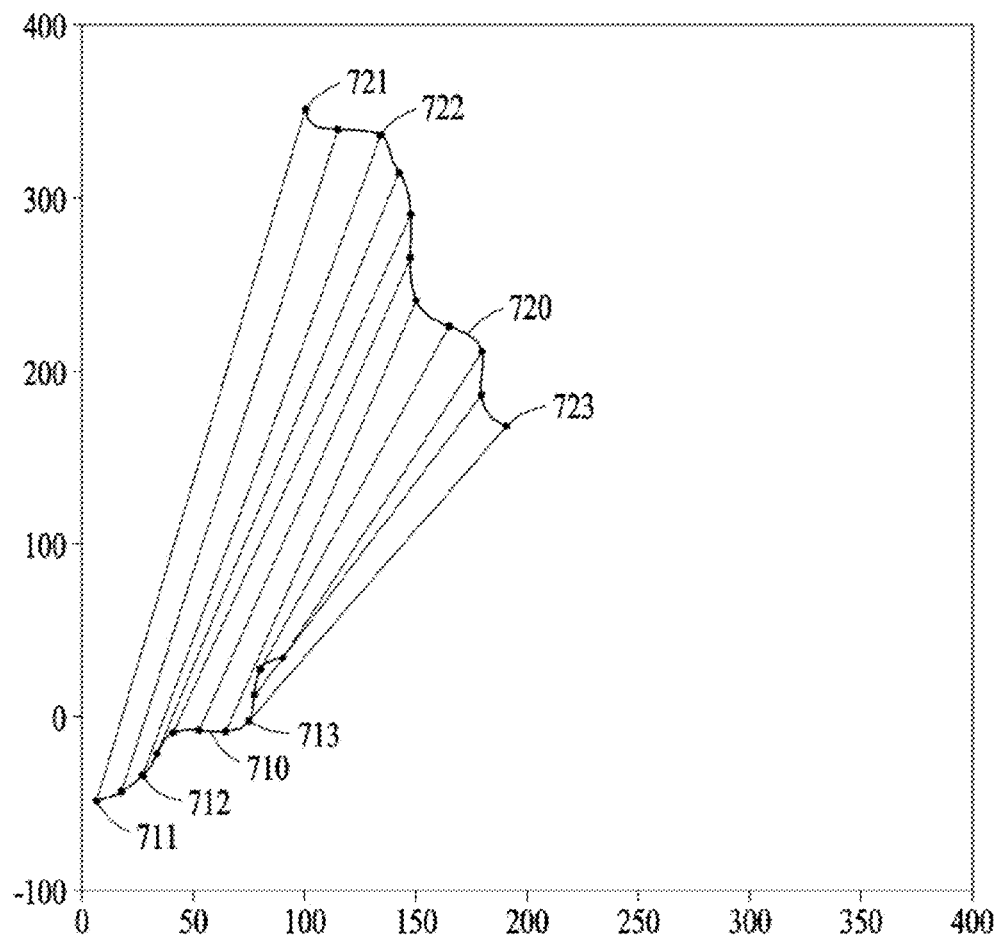
FIGS. 7 to 9 explain a process of calculating distance information between a candidate curve and a source curve by an electronic device.
Figure 8:
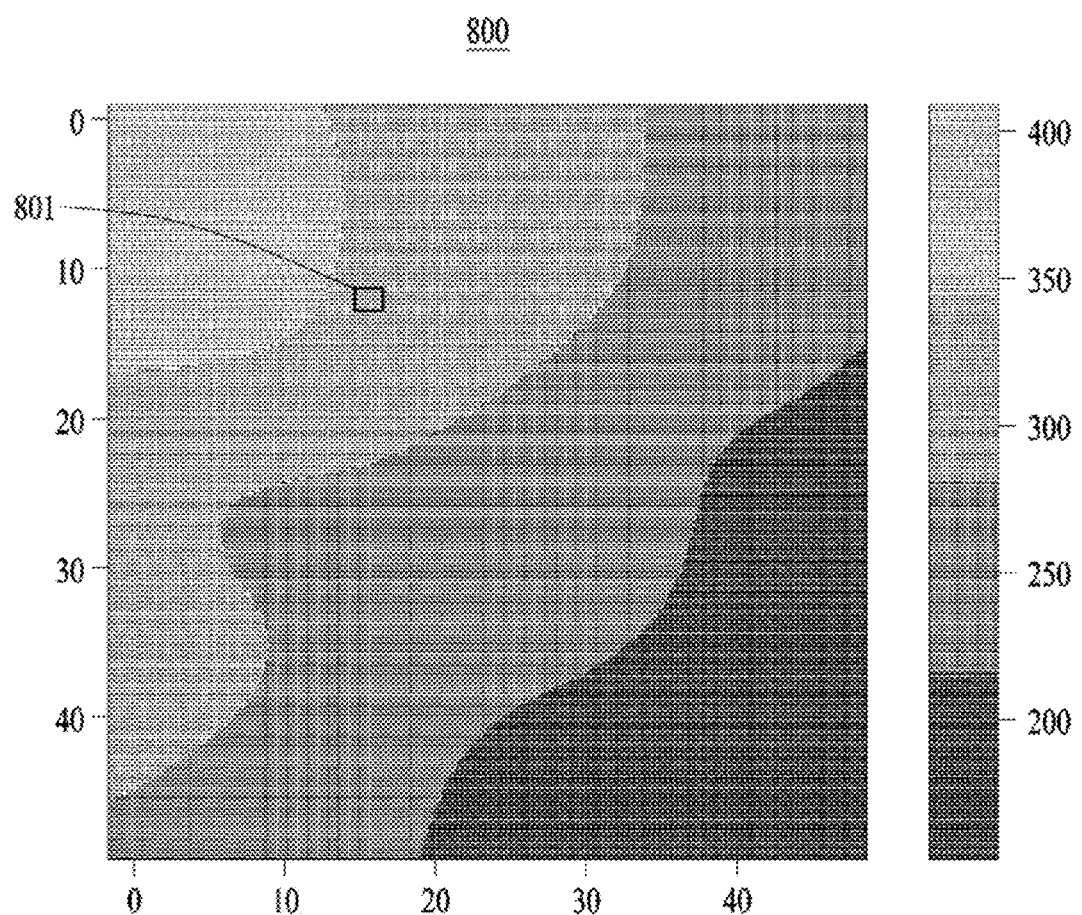
Figure 9:
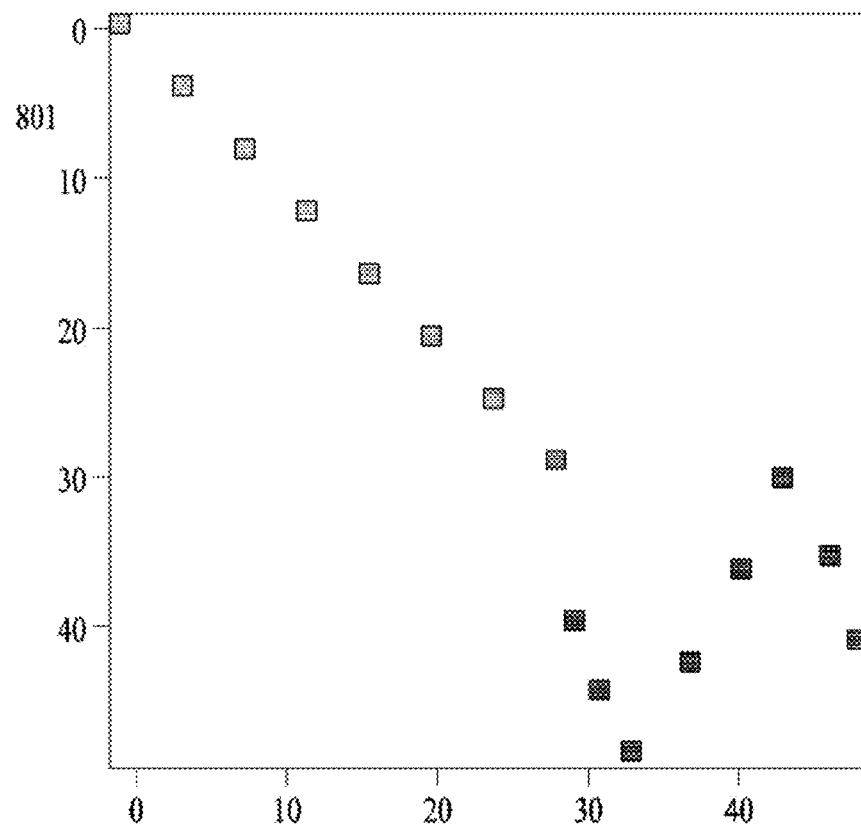

FIGS. 7 to 9 explain a process of calculating distance information between a candidate curve and a source curve by an electronic device. A plurality of candidate curves corresponding to at least a part of the blood vessel may be extracted from the blood vessel image. However, for the convenience of description, in FIGS. 7 to 9, an example of calculating a similarity level of one candidate curve and the source curve will be mainly described.

In FIG. 7, the electronic device according to the example embodiment may match the points sampled from the candidate curve 720 with points sampled from the source curve 710, respectively, so as not to be overlaid. The electronic device may calculate distance information between the candidate curve 720 and the source curve 710 based on a minimum value of a sum of Euclidean distances between matching points in the candidate curve 720 and the source curve 710. The Euclidean distance may indicate a distance on a straight line between two points. To be more specific, the electronic device may calculate an arithmetic mean of the Euclidean distance between the matching points of the candidate curve 720 and the source curve 710 as distance information between the candidate curve 720 and the source curve 710.

For example, it is assumed that the electronic device samples both the source curve 710 and the candidate curve 720 with the first sampling number. The electronic device may match each of the first sampling number of points sampled from the candidate curve 720 to one point of the first sampling number of points sampled from the source curve 710. Points of the source curve 710 matched to each of the points sampled from the candidate curve 720 are different from each other.

FIG. 7 illustrates that points of the candidate curve and points of the source curve matching thereto are connected with a segment. In FIG. 7, the points at both ends connected by the segment indicate matching points among the points sampled from the candidate curve 720 and the source curve 710. Specifically, FIG. 7 illustrates an example that a sum of the Euclidean distance between matched sampled points of the candidate curve 720 and the source curve 710 is minimum. For example, the electronic device may match the first point 721 of the candidate curve 720 to the first point 711 of the source curve 710, match the second point 722 of the candidate curve 720 to the second point 712 of the source curve 710, and match the third point 723 of the candidate curve 720 to the third point 713 of the source curve 710. When the sum of the Euclidean distances between matched sampled points of the candidate curve and the source curve is minimum, the segments obtained by connecting the matched points do not intersect each other.

The electronic device matches the points sampled from the source curve 710 and the points sampled from the candidate curves 720 so as not to be overlaid to calculate the sum of Euclidean distances between matched points in various ways. The electronic device discerns a minimum value of the sum of the Euclidean distances calculated in various ways to calculate distance information between the candidate curve and the source curve based on the discerned minimum value. To be more specific, the electronic device may calculate the distance information by dividing the sums of the Euclidean distances by the sampling number sampled from the candidate curve and the source curve. However, the electronic device may directly match the points of the source curve and the points of the candidate curve so as to make the sum of the Euclidean distances minimum using a more efficient algorithm, which will be described with reference to FIGS. 8 and 9.

FIGS. 8 and 9 explain a method of calculating distance information using a distance matrix by an electronic device according to an example embodiment.

FIG. 8 illustrates a distance matrix 800 calculated using the candidate curve and the source curve by the electronic device. The electronic device may calculate a distance matrix 800 based on Euclidean distances for each of points sampled from the candidate curve and each of points sampled from the source curve.

For example, the electronic device may sample a first sampling number of points from the candidate curve and the source curve. The electronic device may calculate a Euclidean distance between an i-th point sampled from the candidate curve and a j-th point sampled from the source curve. At this time, i and j are natural numbers. The electronic device may represent a Euclidean distance between the i-th point of the candidate curve and the j-th point of the source curve in a component 801 corresponding to an i-th row and a j-th column of the distance matrix 800. Hereinafter, in the specification, a value corresponding to the matrix component may indicate a Euclidean distance represented in the corresponding component.

The electronic device according to the example embodiment may calculate distance information between the candidate curve and the source curve using a Hungarian algorithm in the calculated distance matrix 800. The Hungarian algorithm is an algorithm which solves an assignment problem and has a time complexity of O (N3).

To be more specific, when the electronic device samples the first sampling number of points from the candidate curve and the source curve, the electronic device may select a first sampling number of components from the distance matrix 800 calculated using the Hungarian algorithm. There are various combinations of components of the first sampling number having different rows and columns in the distance matrix 800. In other words, the electronic device may select the first sampling number of components at rows and columns in the distance matrix 800 which are totally different. At this time, the electronic device may select a combination having a minimum sum of values corresponding to the components among combinations of the first sampling number of components at different rows and different columns in the distance matrix 800 using the Hungarian algorithm. FIG. 9 illustrates a distance matrix 900 in which the first sampling number of components having the minimum sum of values corresponding to components selected by the electronic device are represented with colors and the remaining components are represented with white. The electronic device may calculate distance information of the candidate curve and the source curve based on the sum of values corresponding to the first sampling number of selected components. The electronic device may calculate a value obtained by dividing the sum of values corresponding to the first sampling number of selected components by the first sampling number as the distance information.

In other words, the first sampling number of components selected from the distance matrix using the Hungarian algorithm by the electronic device according to the example embodiment may indicate matched points in the candidate curve and the source curve. For example, when the electronic device selects a component in an a-th row and a b-th column from the distance matrix, it is determined that an a-th point of the candidate curve and a b-th point of the source curve may match.

According to the example embodiment, the electronic device may calculate a similarity level using calculated distance information between the candidate curve and the source curve. For example, the electronic device may calculate an inverse number of a value corresponding to the calculated distance information between the candidate curve and the source curve as the similarity level, but the method of calculating a similarity level is not necessarily limited thereto. The smaller the calculated distance information, the higher the similarity level so that the electronic device may determine that the candidate curve and the source curve are similar to each other. In contrast, the larger the calculated distance information, the lower the similarity level so that the electronic device may determine that the candidate curve and the source curve are not similar to each other.

According to the example embodiment, the electronic device may calculate the distance information between each of the plurality of candidate curves extracted from the blood vessel image and the source curve. The electronic device selects a candidate curve having the smallest calculated distance information to determine that there is a guidewire in a blood vessel area corresponding to the selected candidate curve. Since the arrangement of the blood vessel areas in the blood vessel image of the existing frame and the arrangement of the blood vessel areas in the blood vessel image of the target frame are not significantly different due to the heartbeat, the electronic device may determine that the smaller the distance information between the candidate curve and the source curve, the higher the similarity level.

Figure 10:
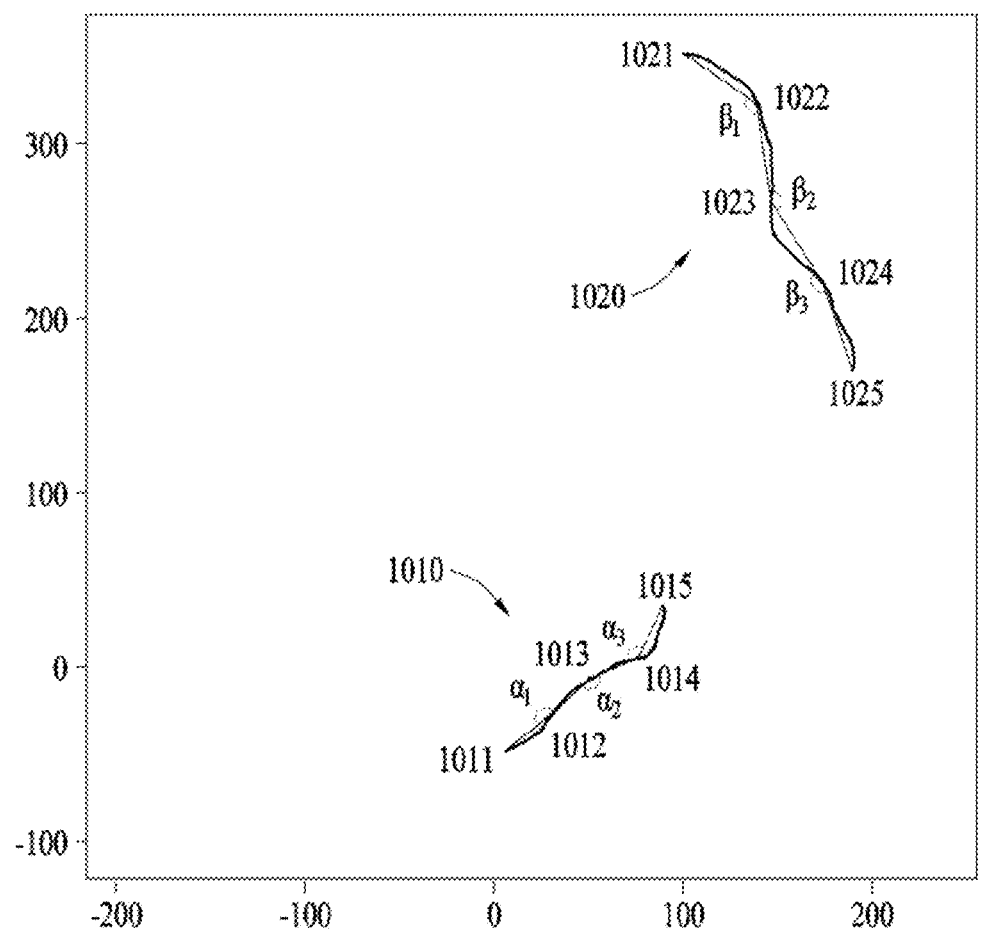
FIG. 10 explains a process of calculating angle information between a candidate curve and a source curve by an electronic device.

FIG. 10 explains a process of calculating angle information between a candidate curve and a source curve by an electronic device. A plurality of candidate curves corresponding to at least a part of the blood vessel may be extracted from the blood vessel image. However, for the convenience of description, in FIG. 10, an example of calculating a similarity level of one candidate curve and the source curve will be mainly described.

The electronic device according to the example embodiment may generate segments by connecting adjacent points among points sampled from the candidate curve 1020 to each other and calculate angles between adjacent segments among the generated segments. Similarly, the electronic device may generate segments by connecting adjacent points among points sampled from the source curve 1010 to each other and calculate angles between adjacent segments among the generated segments. An angle between adjacent segments may refer to an angle formed by adjacent segments which is equal to or smaller than 180 degrees. However, it is not necessarily limited thereto.

For example, in FIG. 10, it is assumed that the electronic device samples five points from a source curve 1010 and a candidate curve 1020. The electronic device connects adjacent points among five points 1011, 1012, 1013, 1014, and 1015 sampled from the source curve 1010 to generate segments. The electronic device may calculate angles $\alpha 1$, $\alpha 2$, and $\alpha 3$ between adjacent segments among the segments generated in the source curve. The electronic device connects adjacent points among five points 1021, 1022, 1023, 1024, and 1025 sampled from the candidate curve 1020 to generate segments. The electronic device may calculate angles $\beta 1$, $\beta 2$, and $\beta 3$ between adjacent segments among the segments generated in the candidate curve. The electronic device may calculate angle information between the candidate curve and the source curve using the angles $\alpha 1$, $\alpha 2$, and $\alpha 3$ calculated from the source curve 1010 and the angles $\beta 1$, $\beta 2$, and $\beta 3$ calculated from the candidate curve 1020.

According to the example embodiment, the electronic device may calculate angle information between the candidate curve and the source curve using one of a cross entropy and Kullback-Leibler divergence from a probability distribution of the angles calculated from the source curve and a probability distribution of the angles calculated from the candidate curve.

The electronic device according to the example embodiment may calculate a probability distribution p of the angles calculated from the source curve and a probability distribution q of the angles calculated from the candidate curve.

For example, the electronic device may calculate the angle information between the candidate curve and the source curve using the cross entropy. The cross entropy is defined by the following Equation 1.

$$H(p, q) = \sum_i p_i \log_2 \frac{1}{q_i} \quad \text{[Equation 1]}$$

In Equation 1, H indicates a cross entropy value, $p_i$ indicates a probability value of a probability distribution of angles calculated from the source curve, and $q_i$ indicates a probability value of a probability distribution of angles calculated from the candidate curve. It may be determined that the smaller the cross entropy value, the more two probability distributions are similar. The electronic device may calculate the cross entropy value as the angle information between the source curve and the candidate curve.

As another example, the electronic device may calculate the angle information between the source curve and the candidate curve using the Kullback-Leibler divergence. The Kullback-Leibler divergence is a function used to calculate a difference between two probability distributions and may be defined by the following Equation 2.

$$D_{KL}(p, q) = \sum_i p(i) \log \frac{p(i)}{q(i)} \quad \text{[Equation 2]}$$

In Equation 2, $D_{KL}$ indicates the Kullback-Leibler divergence value. It may be determined that the smaller the Kullback-Leibler divergence value, the more two probability distributions are similar. The electronic device may calculate the Kullback-Leibler divergence value as the angle information between the source curve and the candidate curve.

According to another example embodiment, the electronic device may smooth the discrete probability distribution of angles calculated from the source curve by performing the kernel density estimation using a kernel function. Similarly, the electronic device may smooth the discrete probability distribution of angles calculated from the candidate curve by performing the kernel density estimation using the kernel function. For example, the kernel function may use Gaussian, Epanechnikov, uniform functions. The electronic device may calculate angle information between the candidate curve and the source curve using one of a cross entropy and Kullback-Leibler divergence from the smoothed probability distribution of the source curve and the smoothed probability distribution of the candidate curve.

According to the example embodiment, the electronic device may calculate a similarity level using calculated angle information between the candidate curve and the source curve. For example, the electronic may calculate an inverse number of a value corresponding to the calculated angle information between the candidate curve and the source curve as the similarity level, but the method of calculating a similarity level is not necessarily limited thereto. The smaller the calculated angle information, the higher the similarity level so that the electronic device may determine that the candidate curve and the source curve are similar to each other. The larger the calculated angle information, the lower the similarity level so that the electronic device may determine that the candidate curve and the source curve are not similar to each other.

According to the example embodiment, the electronic device may calculate the angle information between each of the plurality of candidate curves extracted from the blood vessel image and the source curve. The electronic device selects a candidate curve having the smallest calculated angle information to determine that there is a guidewire in a blood vessel area corresponding to the selected candidate curve. Since the blood vessel areas in the blood vessel image of the existing frame in which the guidewire is disposed and the blood vessel areas in the blood vessel image of the target frame in which the guidewire is disposed have a similar shape, the electronic device may determine that the smaller the angle information between the candidate curve and the source curve, the higher the similarity level.

According to the example embodiment, the electronic device may calculate a similarity level using both the distance information and the angle information between the candidate curve and the source curve. The electronic device according to the example embodiment may determine that a candidate curve which is close to the source curve and has a similar shape is similar to the source curve. In other words, the electronic device may calculate the similarity level of two different curves in consideration of both the position and the shape in the image. The electronic device may calculate the similarity level between the candidate curve and the source curve through various functions based on the distance information and the angle information.

According to the example embodiment, the electronic device may calculate the similarity level based on a value (d×s) obtained by multiplying a value d corresponding to the distance information and a value s corresponding to the angle information. For example, the electronic device may calculate an inverse number of the value obtained by multiplying the value corresponding to the distance information and the value corresponding to the angle information as a similarity level, but it is not necessarily limited thereto.

According to another example embodiment, the electronic device may calculate the similarity level based on a value (d×$e^s$) obtained by multiplying a value d corresponding to the distance information and a square of a value corresponding to angle information of a natural constant e. For example, the electronic device may calculate an inverse number of the value (d×$e^s$) obtained by multiplying the value d corresponding to the distance information and a square of the value corresponding to the angle information of a natural constant e, but it is not necessarily limited thereto.

The electronic device may determine that the larger the calculated similarity level, the more the candidate curve and the source curve are similar, and the smaller the calculated similarity level, the candidate curve and the source curve are not similar to each other.

The electronic device selects the most similar candidate curve to the source curve based on the similarity level calculated from the relationship with the source curve for each of the plurality of candidate curves and may determine that the guidewire is located in the blood vessel area corresponding to the selected candidate curve. To be more specific, the electronic device may determine a candidate curve having the highest similarity level among the similarity levels calculated between each of the candidate curve and the source curve as the most similar candidate curve. The electronic device may determine that the guidewire is located in the blood vessel area corresponding to the candidate curve having the highest similarity level.

According to the example embodiment, the electronic device overlays the guidewire in the blood vessel area which is determined that the guidewire is located to visualize the guidewire together with the blood vessel image. Further, according to the example embodiment, the electronic device may further include a driver which drives the guidewire. The electronic device drives the driver based on the blood vessel area determined that the guidewire is located to move the tip of the guidewire toward the destination area of the guidewire.

Further, according to the example embodiment, the electronic device may calculate the similarity levels respectively by sampling the candidate curve and the source curve with various sampling numbers. The electronic device may select a candidate curve which is the most similar to the source curve using the plurality of calculated similarity levels. For example, the electronic device may sample a first sampling number of points from each of the candidate curve and the source curve. The electronic device may calculate a first similarity level between the candidate curve and the source curve based on the first sampling number of points sampled from the candidate curve and a first sampling number of points sampled from the source curve by the above-described method. Further, the electronic device may sample a second sampling number of points which is different from the first sampling number, from the candidate curve and the source curve, respectively. The electronic device may recalculate a second similarity level between the candidate curve and the source curve based on the second sampling number of points sampled from the candidate curve and a second sampling number of points sampled from the source curve. The electronic device selects a candidate curve which is the most similar to the source curve, based on at least one of the first similarity level and the second similarity level calculated above to estimate a position of the guidewire. For example, the electronic device calculates an arithmetic mean of the first similarity level and the second similarity level as the final similarity level between the candidate curve and the source curve and may select a candidate curve having the highest similarity level.

As a method of the related art to compare the similarity levels of two curves, there is a method of calculating the similarity levels of two curves based on a magnitude of a transformation matrix required for registration of two curves using an iterative closest point algorithm. However, this method has a disadvantage of having to undergo a process of iteratively finding more significant point pairs. When the similarity between the curves is determined by this method, a large computational amount is required so that it is difficult to use this method in an environment in which a fast operation such as real-time execution is requested. As another method, there is a method of calculating the similarity level between two curves using a curvature comparison method that can be used when the curves are mathematically parameterized. However, an accurate curvature cannot be calculated from a discrete curve formed by a two-dimensional point array. In this case, even though there may be a method using an approximation, this has a disadvantage in terms of computation speed because an iterative approach is also forced. In contrast, the similarity level determining method performed by the electronic device according to the example embodiment may calculate the similarity level of two different curves based on a value which reflects the distance information and the angle information. The method according to the example embodiment may achieve the similarity level by one computational process so that it does not require a large computational amount to calculate a similarity level for a curve which changes in real-time. The method according to the example embodiment considers an overall shape of the curve to obtain a robust value for the change of the same curve which is simply rotated, enlarged, or reduced. The method according to the example embodiment may be utilized to calculate the similarity level between structures formed by a plurality of curves or perform the image registration.

Figure 11:
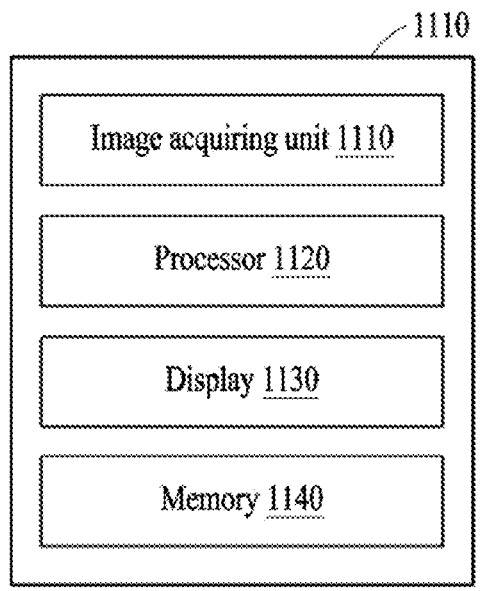
FIG. 11 is a block diagram explaining a structure of an electronic device according to an example embodiment.

FIG. 11 is a block diagram explaining a structure of an electronic device according to an example embodiment.

The electronic device 1100 may include an image acquiring unit 1110, a processor 1120, a display 1130, and a memory 1140. The electronic device 1100 may also be referred to as a guidewire detecting device.

The image acquiring unit 1110 may acquire a blood vessel image of a reference frame and a blood vessel image of a target frame. The image acquiring unit 1110 according to the example embodiment may acquire a coronary angiography (CAG) image of the reference frame and the target frame as blood vessel images of the reference frame and the target frame. The image acquiring unit 1110 may capture a blood vessel image or receive a blood vessel image from an external imaging device.

The processor 1120 may acquire a blood vessel image of the reference frame. The processor 1120 may extract a candidate curve corresponding to at least a part of the blood vessel from a blood vessel image of the reference frame. The processor 1120 may acquire a blood vessel image of the target frame. The processor 1120 may extract a source curve corresponding to the guidewire from the blood vessel image of the target frame. The processor 1120 may sample the same sampling number of points from the candidate curve and the source curve. The processor 1120 may calculate a similarity level between the candidate curve and the source curve based on the points sampled from the candidate curve and the points sampled from the source curve. The processor 1120 may determine whether the candidate curve and the source curve are similar, based on the calculated similarity level. However, the operation of the processor 1120 is not limited to the operation described above, but the processor may perform the operations described above in FIGS. 1 to 10.

The display 1130 may overlay the guidewire with the blood vessel area corresponding to the selected candidate curve to visualize the guidewire together with the blood vessel image.

The memory 1140 may temporarily and/or permanently store data and/or information required to perform the guidewire detection method.

The example embodiments described above may be implemented by a hardware component, a software component, and/or a combination of the hardware component and the software component. For example, the device, the method, and the components described in the example embodiments may be implemented, for example, using a general purpose computer or a special purpose computer such as a processor, a controller, an arithmetic logic unit (ALU), a digital signal processor, a microcomputer, a field programmable gate array (FPGA), a programmable logic unit (PLU), a microprocessor, or any other device which executes or responds instructions. The processing device may perform an operating system (OS) and a software application which is executed on the operating system. Further, the processing device may access, store, manipulate, process, and generate data in response to the execution of the software. For ease of understanding, it may be described that a single processing device is used, but those skilled in the art may understand that the processing device includes a plurality of processing elements and/or a plurality of types of processing element. For example, the processing device may include a plurality of processors or include one process and one controller. Further, another processing configuration such as a parallel processor may be allowed.

The software may include a computer program, a code, an instruction, or a combination of one or more of them and configure the processing device to be operated as desired or independently or collectively command the processing device. The software and/or data may be permanently or temporarily embodied in an arbitrary type of machine, component, physical device, virtual equipment, computer storage medium, or device, or signal wave to be transmitted to be interpreted by a processing device or provide command or data to the processing device. The software may be distributed on a computer system connected through a network to be stored or executed in a distributed manner. The software and data may be stored in a computer readable recording medium.

The method according to the example embodiment may be implemented as a program command which may be executed by various computers to be recorded in a computer readable medium. The computer readable medium may include the program instruction, a data file, or a data structure alone or in combination and the program instruction stored in the medium may be specifically designed and configured for the example embodiment or known to be available to those skilled in the art of computer software. Examples of the computer readable recording medium include magnetic media such as a hard disk, a floppy disk, or a magnetic tape, optical media such as a CD-ROM or a DVD, magneto-optical media such as a floptical disk, and a hardware device which is specifically configured to store and execute the program command such as a ROM, a RAM, and a flash memory. Examples of the program command include not only a machine language code which is created by a compiler but also a high level language code which may be executed by a computer using an interpreter.

The hardware device may operate as one or a plurality of software modules in order to perform the operation of the example embodiment and vice versa.

As described above, although example embodiments have been described by limited drawings, those skilled in the art may apply various technical modifications and changes based on the above description. For example, even when the above-described techniques are performed by different order from the described method and/or components such as systems, structures, devices, or circuits described above are coupled or combined in a different manner from the described method or replaced or substituted with other components or equivalents, the appropriate results can be achieved.

Therefore, other implements, other embodiments, and equivalents to the claims are within the scope of the following claims.

What is claimed is:

1. A method for determining a similarity between curves performed by an electronic device, the method comprising:
    Inserting medical tool with a guidewire in to a blood vessel;
    acquiring images of a blood vessel with guidewire via a blood vessel imaging device;
    extracting a candidate curve corresponding to at least a part of the blood vessel and a source curve corresponding to the guidewire from the blood vessel image;
    sampling the same sampling number of points from each of the candidate curve and the source curve;
    calculating a similarity level between the candidate curve and the source curve based on the points sampled from the candidate curve and the points sampled from the source curve; and
    determining whether the candidate curve and the source curve are similar, based on the calculated similarity level, wherein the calculating of a similarity level includes:
    matching points sampled from the candidate curve to points sampled from the source curve so as not to be overlaid; and
    calculating distance information between the candidate curve and the source curve based on a minimum value of a sum of Euclidean distances between matched points;
    displaying the candidate curves corresponding to the extracted at least the part of the blood vessel.

2. The method of claim 1, wherein the extracting includes:
    extracting the candidate curve corresponding to the at least a part of the blood vessel from a blood vessel image of a reference frame; and extracting the source curve corresponding to the guidewire from a blood vessel image of a target frame.

3. The method of claim 1, wherein the calculating of a similarity level includes:
sampling points from the candidate curve and the source curve so as to have the same interval between adjacent points.

4. The method of claim 1, wherein the calculating of a similarity level includes:
calculating an arithmetic mean of Euclidean distances between matched points as the distance information between the candidate curve and the source curve.

5. The method of claim 1, wherein the calculating of a similarity level includes:
calculating a distance matrix based on a Euclidean distance for each of the points sampled from the candidate curve and each of the points sampled from the source curve; and
calculating the distance information from the calculated distance matrix based on the Hungarian algorithm.

6. A method for determining a similarity between curves performed by an electronic device, the method comprising:
Inserting medical tool with a guidewire in to a blood vessel;
acquiring images of a blood vessel with guidewire via a blood vessel imaging device;
extracting a candidate curve corresponding to at least a part of the blood vessel and a source curve corresponding to the guidewire from the blood vessel image;
sampling the same sampling number of points from each of the candidate curve and the source curve;
calculating a similarity level between the candidate curve and the source curve based on the points sampled from the candidate curve and the points sampled from the source curve; and
determining whether the candidate curve and the source curve are similar, based on the calculated similarity level, wherein the calculating of a similarity level includes:
generating segments by connecting adjacent points among points sampled from the candidate curve and calculating angles between adjacent segments among the generated segments;
generating segments by connecting adjacent points among points sampled from the source curve and calculating angles between adjacent segments among the generated segments; and
calculating angle information between the candidate curve and the source curve using the angles calculated from the candidate curve and the angles calculated from the source curve;
displaying the candidate curves corresponding to the extracted at least the part of the blood vessel.

7. The method of claim 6, wherein the calculating of a similarity level includes:
calculating the angle information using one of cross entropy and Kullback-Leibler divergence from a probability distribution of the angles calculated from the candidate curve and a probability distribution of the angles calculated from the source curve.

8. The method of claim 1, further comprising:
selecting a candidate curve which is the most similar to the source curve based on the calculated similarity level and determining that the guidewire is located in a blood vessel area corresponding to the selected candidate curve.

9. The method of claim 8, further comprising:
visualizing the guidewire together with the blood vessel image by overlaying the guidewire with the blood vessel area determined that there is the guidewire.

10. An electronic device for use in combination with a medical tool comprising a guidewire configured for Inserting in to a blood vessel and images of the blood vessel with the guidewire acquired via a blood vessel imaging device, the electronic device comprising:
a processor configured to extract a candidate curve corresponding to at least a part of the blood vessel and a source curve corresponding to the guidewire from the blood vessel image, sample the same sampling number of points from each of the candidate curve and the source curve, calculate a similarity level between the candidate curve and the source curve based on the points sampled from the candidate curve and the points sampled from the source curve, and determine whether the candidate curve and the source curve are similar, based on the calculated similarity level, wherein the processor is further configured to match points sampled from the candidate curve to points sampled from the source curve so as not to be overlaid and calculate distance information between the candidate curve and the source curve based on a minimum value of a sum of Euclidean distances between matched points;
a display configured for displaying the candidate curves corresponding to the extracted at least the part of the blood vessel that is acquired via the blood vessel imaging device with the guidewire.

11. The electronic device of claim 10, wherein the processor is further configured to extract the candidate curve corresponding to the at least a part of the blood vessel from a blood vessel image of a reference frame, and extract the source curve corresponding to the guidewire from a blood vessel image of a target frame.

12. The electronic device of claim 10, wherein the processor is further configured to sample points from the candidate curve and the source curve so as to have the same interval between adjacent points.

13. The electronic device of claim 10, wherein the processor is configured to calculate a distance matrix based on a Euclidean distance for each of the points sampled from the candidate curve and each of the points sampled from the source curve and calculate the distance information from the calculated distance matrix based on the Hungarian algorithm.

14. The electronic device of claim 10, wherein the processor is configured to generate segments by connecting adjacent points among points sampled from the candidate curve and calculate angles between adjacent segments among the generated segments, generate segments by connecting adjacent points among points sampled from the source curve and calculate angles between adjacent segments among the generated segments, and calculate angle information between the candidate curve and the source curve using the angles calculated from the candidate curve and the angles calculated from the source curve.

* * * * *